(12) United States Patent
Mayer

(10) Patent No.: US 12,400,764 B2
(45) Date of Patent: Aug. 26, 2025

(54) DIGITAL PLATFORM FOR INFECTIOUS DISEASE TRACKING AND TESTING SUPPORT

(71) Applicant: Safe Health Systems, Inc., Scottsdale, AZ (US)

(72) Inventor: Ken Mayer, Los Angeles, CA (US)

(73) Assignee: Safe Health Systems, Inc., Phoenix, AZ (US)

( * ) Notice: Subject to any disclaimer, the term of this patent is extended or adjusted under 35 U.S.C. 154(b) by 194 days.

(21) Appl. No.: 18/032,443

(22) PCT Filed: Oct. 19, 2021

(86) PCT No.: PCT/US2021/055582
§ 371 (c)(1),
(2) Date: Apr. 18, 2023

(87) PCT Pub. No.: WO2022/086940
PCT Pub. Date: Apr. 28, 2022

(65) Prior Publication Data
US 2023/0411016 A1      Dec. 21, 2023

Related U.S. Application Data

(60) Provisional application No. 63/114,970, filed on Nov. 17, 2020, provisional application No. 63/093,612, filed on Oct. 19, 2020.

(51) Int. Cl.
| | | |
|---|---|---|
| G16H 50/30 | (2018.01) | |
| G16H 10/40 | (2018.01) | |
| G16H 40/67 | (2018.01) | |
| G16H 50/80 | (2018.01) | |

(52) U.S. Cl.
CPC .......... *G16H 50/30* (2018.01); *G16H 10/40* (2018.01); *G16H 40/67* (2018.01); *G16H 50/80* (2018.01)

(58) Field of Classification Search
None
See application file for complete search history.

(56) References Cited

U.S. PATENT DOCUMENTS

| | | | |
|---|---|---|---|
| 2017/0024531 A1* | 1/2017 | Malaviya | G16H 50/30 |
| 2020/0098461 A1* | 3/2020 | Macoviak | G06Q 30/018 |
| 2020/0184153 A1* | 6/2020 | Bongartz | A01G 9/249 |

OTHER PUBLICATIONS

Jian et al. ("Real-time surveillance of infectious diseases: Taiwan's experience." Health security 15.2 (2017): 144-153 (Year: 2017).*

* cited by examiner

*Primary Examiner* — Christopher B Tokarczyk
(74) *Attorney, Agent, or Firm* — COATS & BENNETT, PLLC

(57) ABSTRACT

This specification discloses techniques for assessing an individual's risk of exposure to a pathogen for an infectious disease, and related testing methods.

18 Claims, 4 Drawing Sheets

DIGITAL PLATFORM FOR INFECTIOUS DISEASE TRACKING AND TESTING SUPPORT

CROSS-REFERENCE TO RELATED APPLICATIONS

This application claims the benefit of U.S. Provisional Application Ser. No. 62/795,230, filed Nov. 17, 2020, and U.S. Provisional Application Ser. No. 63/093,612, filed Oct. 19, 2020. The disclosures of the prior applications are considered part of (and is incorporated by reference in) the disclosure of this application.

FIELD OF THE DISCLOSURE

This disclosure relates to digital health platforms, and more specifically to computer-based technologies for assessing an individual's risk of exposure to a pathogen for an infectious disease, and related testing methods.

BACKGROUND

The severe acute respiratory syndrome coronavirus 2 (SARS-CoV-2) virus was first discovered in December 2019. The virus, which serves as the underlying mechanism of the acute respiratory disease COVID-19, is highly infectious and quickly spread to cause a global pandemic by March 2020. Public health experts have implemented various strategies to contain and mitigate the spread of the virus in order to limit the rate of new infections. For example, new outbreaks have been identified through testing and contact tracing methods, which involve identifying persons who have tested positive for the virus and subsequently identifying additional persons who have interacted with those who tested positive. The identified persons can be quarantined, tested, or both, to ensure they do not spread the virus to others during the period of time when they could be infected. Nonetheless, contact tracing can be a difficult task since individuals often do not recall all or many of the people with whom they have interacted over a period of time. Moreover, it can be burdensome for persons who present with symptoms of COVID-19 or other infectious diseases to be tested, obtain test kits, or obtain specimen collection devices.

SUMMARY

This specification describes computer-based systems, methods, devices, and other techniques for assessing an individual's likelihood of exposure to an infectious agent. The techniques can be integrated into a digital health platform that includes one or more client-side applications (e.g., mobile device applications) and one or more server-side applications. In some embodiments, the client-side application uses location data and short-range wireless communications to track interactions between the user and others based on detections of proximity to mobile devices belonging to others. Upon receiving indications that the user has interacted (e.g., been in close proximity to) one or more individuals that have been identified as having been exposed to the infectious agent (or likely exposed to the infectious agent), the platform can assess the interactions and quantify the risk of the interaction. The quantified risk can be expressed as a score that indicates, for example, a likelihood that the user was exposed to the infectious agent such that the user could become infected. The amount of risk associated with interactions may be weighted based on attributes of the locations where the interactions occurred. If a person requires testing, the platform may provide an efficient solution for the user to obtain an appropriate test kit by inputting relevant information to a mobile application that allows a provider or pharmacist to easily select/assemble an appropriate kit that can be picked up at a designated location.

Some implementations of the subject matter disclosed herein include methods for assessing a risk of exposure by a first individual to an infectious agent. The methods can include identifying, by a computing system, a first interaction between the first individual and a second individual based on an indication that a mobile device of the first individual was in a proximity of the second individual. The system obtains context data that describes a context of the first interaction between the first individual and the second individual. The system receives an indication that the second individual was exposed to the infectious agent. Using the context data, a first interaction risk score is determined that indicates an estimated risk of exposure by the first individual to the infectious agent as a result of the first interaction between the first individual and the second individual. Using the first interaction risk score, or another risk score derived at least in part from the first interaction risk score, the system can trigger at least one of (i) an alert related to the risk of exposure by the first individual to the infectious agent or (ii) a recommended action for the individual related to the first individual's possible exposure to the infectious agent.

These and other implementations can further include one or more of the following features.

A second interaction can be identified between the first individual and the second individual. Second context data can be obtained that describes a context of the second interaction between the first individual and the second individual. Using the second context data, a second interaction risk score can be determined that indicates an estimated risk of exposure by the first individual to the infectious agent as a result of the second interaction between the first individual and the second individual. Multiple interaction risk scores, including the first interaction risk score and the second interaction risk score, can be aggregated to determine an aggregated interaction risk score. Using the aggregated interaction risk score, the system can trigger at least one of (i) the alert related to the risk of exposure by the first individual to the infectious agent or (ii) the recommended action for the individual related to the first individual's possible exposure to the infectious agent.

Multiple interaction risk scores, including the first interaction risk score and additional interaction risk scores that relate to interactions between the first individual and additional individuals other than the second individual who were exposed to the infectious agent, can be aggregated to determine an aggregated interaction risk score. Using the aggregated interaction risk score, the system can trigger at least one of (i) the alert related to the risk of exposure by the first individual to the infectious agent or (ii) the recommended action for the individual related to the first individual's possible exposure to the infectious agent.

The indication that the second individual was exposed to the infectious agent can include an indication that the second individual has been infected by the infectious agent.

The context data that describes the context of the first interaction between the first individual and the second individual can include mapping data that identifies one or more attributes of a location where the first interaction occurred. The mapping data can identify at least one of a zoning classification for an area corresponding to the location where the first interaction occurred or a facility classification for a facility corresponding to the location where the first interaction occurred, wherein the first interaction risk score is weighted based on the zoning classification or the facility classification.

The context data can indicate a physical distance between the first individual and the second individual during the first interaction.

The context data can indicate a time duration of the first interaction between the first individual and the second individual.

The context data can indicate a parameter that is based on when the second individual was exposed to the infectious agent, when the second individual tested positive for being infected by the infectious agent, or when the second individual presented one or more symptoms of being infected by the infectious agent.

The context data can indicate a health profile for the first individual, the health profile including at least one of demographic information for the first individual, an indication of co-morbidities exhibited by the first individual, or a health history of the first individual.

The computing system can include the first mobile device or the second mobile device.

The first mobile device can be a smartphone, a tablet computing device, a notebook computer, or a smartwatch.

Identifying the first interaction between the first individual and the second individual can include detecting a wireless signal emitted by the second mobile device, and correlating the wireless signal with the second mobile device or the second individual.

Some implementations of the subject matter disclosed herein include methods for processing test kits. The methods can include actions of receiving, by a computing device, user input specifying bodily health symptoms that have presented in a person; transmitting, from the computing device and to a remote computing system, data indicating the specified bodily health symptoms that have presented in the person; receiving, by the computing device and from the remote computing system, information identifying an order for a particular test kit for use in testing for a medical condition that was selected based on the data indicating the specified bodily health symptoms that have presented in the person; and rendering a visual representation of the order for the particular test kit on a display of the computing device that can be scanned by an optical reader, wherein a second system retrieves the particular test kit to fulfill the order as a result of scanning the visual representation of the order.

These and other implementations can further include one or more of the following features.

The computing device can include a smartphone, a tablet computing device, a notebook computer, a desktop computer, or a wearable computing device.

The visual representation of the order can be formatted and rendered and as a barcode. The barcode can be a quick response (QR) code.

The remote computing system can be configured to select the particular test kit from among a set of candidate test kits based on identifying matches between the specified bodily health symptoms of the person and one or more systems that were pre-defined as being associated with a medical condition for which the particular test kit is configured to test.

The medical condition can be influenza or COVID-19.

The second system can include an automated kiosk.

Aspects of the present subject matter include one or more non-transitory computer-readable media. The media can have instructions stored thereon that, when executed by one or more processors, cause the one or more processors to perform any of the methods and processes disclosed herein. Yet additional aspects include a computing system having the one or more processors and computer-readable media storing such instructions.

Additional features and advantages will be apparent from the description, the drawings, and the claims.

BRIEF DESCRIPTION OF THE DRAWINGS

Like reference numbers and indications in the various drawings indicate like elements.

DETAILED DESCRIPTION

Computer-based systems, methods, devices, and other techniques are provided herein for assessing an individual's likelihood of exposure to an infectious agent. The techniques can be integrated into a digital health platform that includes one or more client-side applications (e.g., mobile device applications) and one or more server-side applications.

Figure 1:
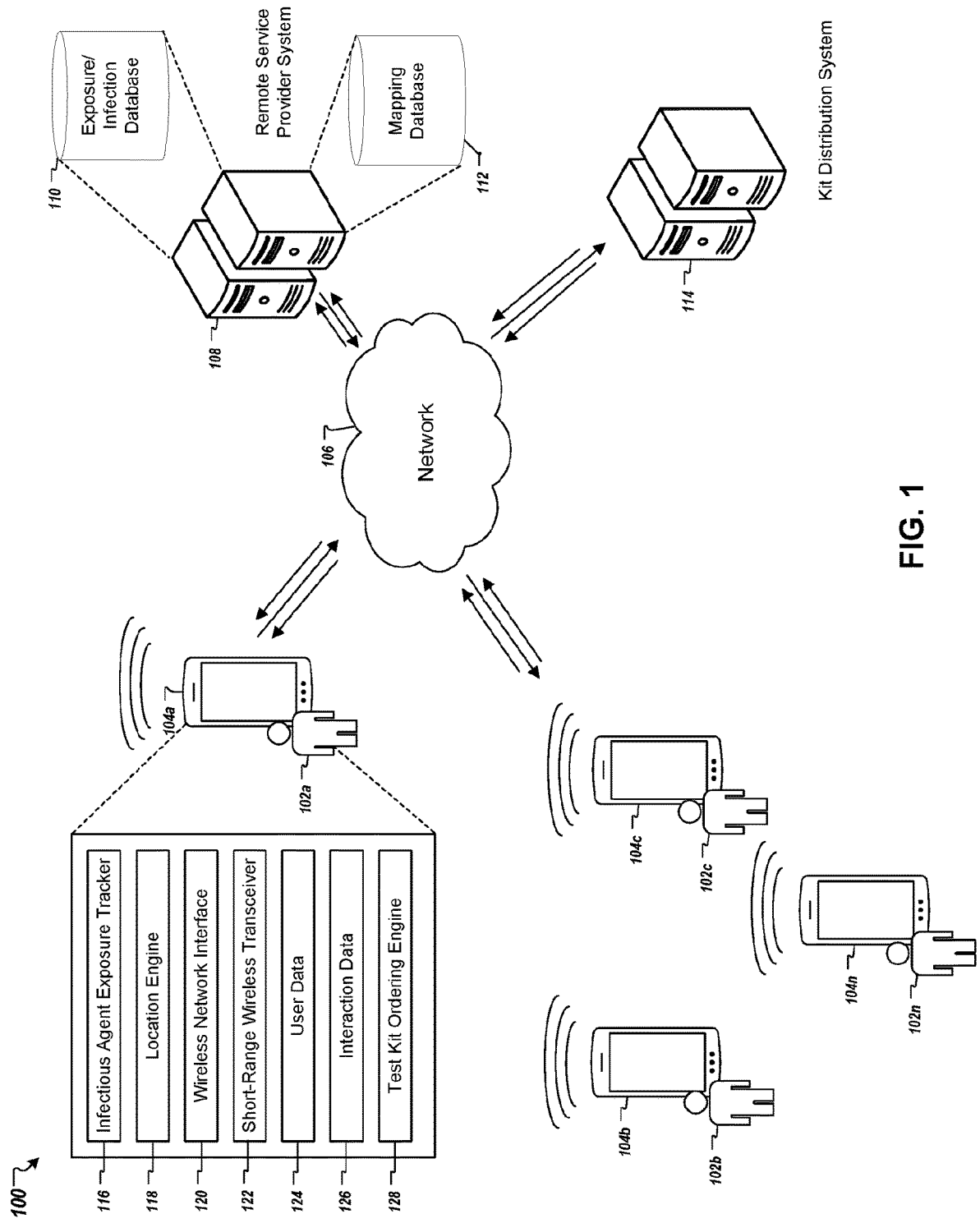
FIG. 1 is a block diagram of an example computing environment of a platform for infectious disease tracking and testing support.

Referring to FIG. 1, a block diagram is shown of an example computing environment 100 for a digital platform that facilitates tracking of a user's possible exposure to an infectious agent (e.g., a viral or bacterial agent). Various computing devices and/or systems are provided in the environment, including mobile devices 104$a$-$n$ belonging to users 102$a$-$n$, respectively, a remote service provider system 108, and a kit distribution system 114. The mobile devices 104$a$-$n$ are typically devices that are frequently carried on the person of the user such as a smartphone, a tablet computer, a smartwatch, or other wearable device. In some examples, the mobile devices 104$a$-$n$ may be a laptop computer or other suitable device that the user carries on himself or herself frequently, or even occasionally. Systems 108 and 114 may each be implemented on one or more computers in one or more locations. The mobile devices 104$a$-$n$, remote service provider system 108, and kit distribution system 114 may interact and communicate with each other, and with other computers, over one or more networks 106, e.g., the Internet or a local area network.

The mobile devices 104$a$-$n$ are each equipped with software, hardware, firmware, or a combination of them, for implementing the digital health platform. Capabilities employed by the platform can include one or more of an infectious agent tracker 116, a location engine 118, a wireless network interface 120, a short-range wireless transceiver 122, a user data repository 124, an interaction data repository 126, and a test kit ordering engine 128. In general, the tracker 116 is configured to track interactions between a first user 102$a$ of the mobile device 104$a$ with other (second) users 102$b$-$n$ of mobile devices 104$b$-$n$. The tracker 116 can use short-range wireless transceiver 122 (e.g., a BLUETOOTH transceiver) to emit beacons/signals that other mobile devices 104$b$-$n$ can detect when the devices are in range of each other, where the emitted beacon or signal is encoded with information uniquely associated with the mobile device 104a and/or user 102a. Likewise, the first device 104a can detect unique beacons/signals emitted by the other mobile devices 104b-n to detect interactions with other users. The location engine 118 is configured to track the current location of the mobile device 104a, and to record locations where identified interactions occur between the user 102a and other users. In some implementations, location engine 118 comprises a global positioning system (GPS) module that determines the geographic coordinates of the device 104a. Wireless network interface 120 permits communication over network 106 or a wireless network adjacent to network 106, such as a WI-FI network interface or a 3G, 4G, or 5G network interface. The user data repository 124 stores information about the user 102a, while interaction data repository 126 stores information about interactions detected by the tracker 116. Test kit ordering engine 128 is configured to facilitate the user 102a in acquiring a medical test kit to test for an identified disease or medical condition. Remote service provider system 108 includes or interfaces with databases including exposure/infection database 110 and/or mapping database 112.

Figure 2:
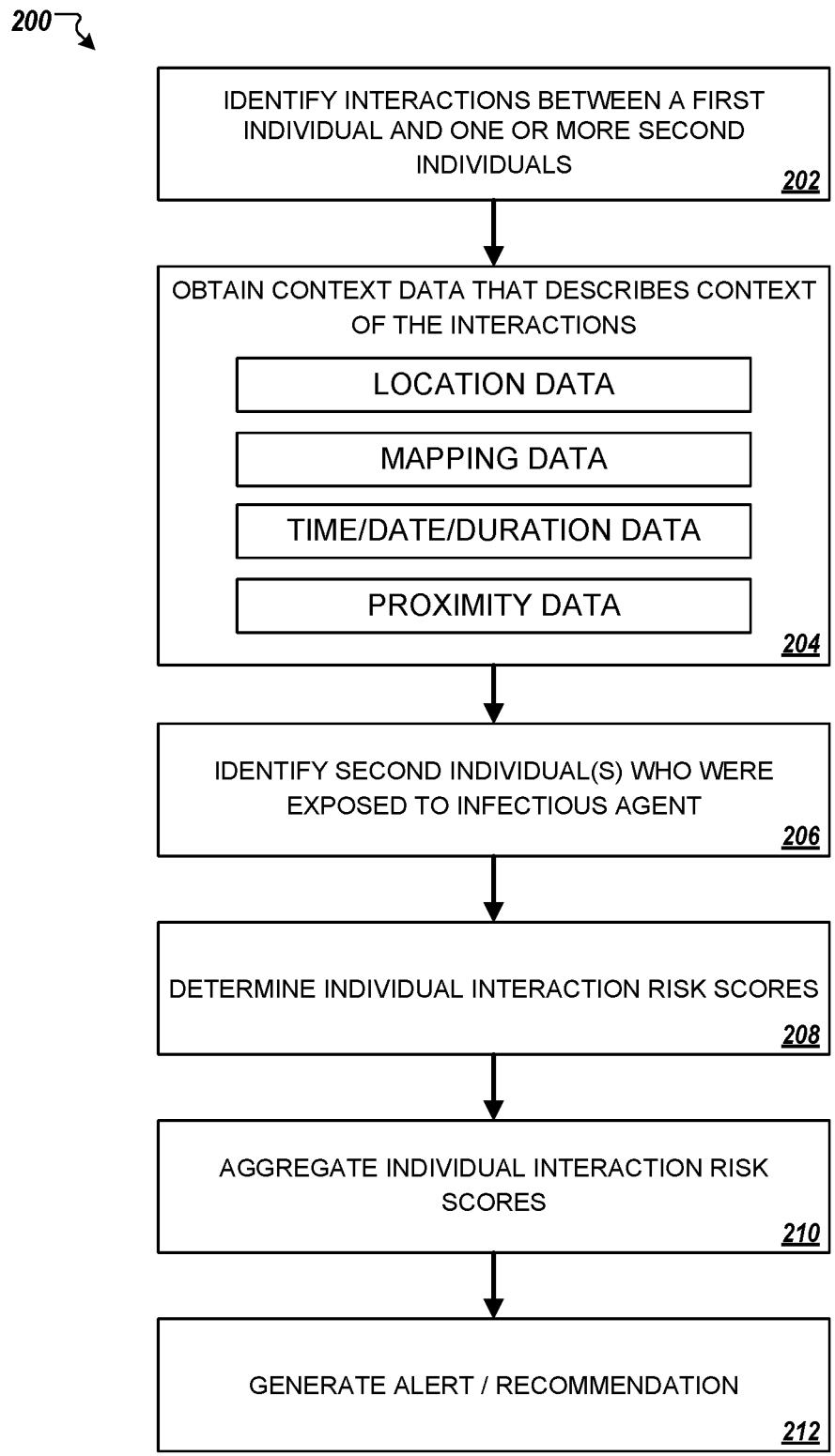
FIG. 2 is a flowchart of an example process for assessing an individual's risk of exposure to an infectious agent.

FIG. 2 is a flowchart of an example process 200 for assessing an individual's risk of exposure to an infectious agent. In some implementations, the process 200 can be carried out in whole or in part by systems and devices akin to those depicted in the computing environment 100 of FIG. 1. In particular, the process 200 can assess the risk of exposure of a first individual to an infectious agent (e.g., a viral or bacterial agent that underlie diseases such as COVID-19, whooping cough, or influenza). The system identifies interactions between the first individual and one or more second individuals (202). An interaction is registered, for example, when the first individual's mobile device detects that it is in proximity of a second individual's mobile device, e.g., as a result of monitoring for short-range wireless beacons/signals that uniquely identify the second individual's mobile device. The short-range wireless beacons/signals can be BLUETOOTH beacons/signals, in some examples. The monitoring can be performed so as to protect the identity and personal data of each user, such as through use of anonymization and cryptographic techniques.

For each interaction with a second user's mobile device, the system determines context data that describes the interaction (204). The context can include an indication of where the interaction occurred (e.g., GPS/geographical coordinates), a time, date, and/or duration of the interaction, and an indication of the proximity of the mobile device of the first and second individual during the interaction. In some implementations, the context further includes mapping data that describes one or more attributes of the location where the interaction occurred. For example, the mapping data can contain zoning information characterizing a public or private zoning classification for the location where the interaction occurred (e.g., industrial, light industrial, commercial, light commercial, agricultural, single-family residential, multi-unit residential, school). Additionally, or alternatively, the mapping data can contain a facility-type classification indicating a type of the facility where the interaction occurred (e.g., office building, school, manufacturing plant, meat processing plant, hospital, single-family residence, apartment building, public park, church, restaurant, stadium, concert venue). The zoning classification, facility-type classification, or both can be determined by referencing maps containing zoning and/or facility-type information against the location data indicating where the location of the interaction occurred. Context data for each interaction can be stored at the first user's mobile device or at the remote service system.

The system can obtain indications of one or more second individuals(s) who were exposed to (e.g., infected by) the infectious agent (206). For example, through an application on the mobile device, a user who is confirmed to have been exposed to the infectious agent such that he or she is possibly infectious (e.g., as a result of testing positive for being infected by the agent) can enter a confirmation that he or she has been exposed. A third-party such as a testing company or medical service provider may also enter the confirmation on behalf of the second individual. The remote service system can update the second individual's positive status in the infection/exposure database, and then notifies each other mobile device of users who have interacted with the second individual within a defined period of time corresponding to a start of when the second individual could have exposed others to the agent. The first mobile device of the first individual receives this notification at stage 206.

For each interaction with an individual who has had a positive exposure to the agent (which could be limited to each interaction with an individual who has tested positive as infected by the agent), the system determines a per-interaction risk score indicating the level of risk estimated for the interaction that the first individual could be exposed/infected by the agent as a result of the interaction (208). The level of risk assigned to each interaction can be weighted by information about the context of the interaction. Interactions within some zoning classifications may be assigned a higher risk than equivalent interactions within other zoning classifications. For instance, interactions within a dense commercial district or within a home may be weighted with higher risk of exposure than interactions within office buildings where interactions are naturally separated by offices or cubicles and the workspace has a relatively low density of people. Similarly, different facility-type classifications may result in relatively higher or lower risk assessments per interaction. Proximity data can affect the risk score as well, as closer proximity interactions are typically high risk than farther proximities. The duration of the interaction and the time since the interaction can also impact the risk assessment.

The system then aggregates the per-interaction (individual) risk scores to determine an aggregated risk score that reflects the overall likelihood the first individual has been exposed to the infection agent (210). Based on the aggregated risk score, the system can determine whether to alert one or more stakeholders including the first individual, a medical provider, or both (212). The alert can be, for example, an application programming interface (API) call to the first individual's mobile device that prompts the mobile device to display a notification or alert to the user regarding the user's likely exposure to the agent. In some cases, the alert (or recommendation) is only generated when the aggregated risk score is sufficiently high, e.g., meets or exceeds a pre-defined threshold score. In some implementations, a recommendation can be provided to the first individual via display on the mobile device instructing the first individual to take one or more actions such as seek medical attention, obtain a diagnostic test, self-isolate/self-quarantine, or a combination of these. Efficient use of healthcare resources can be made by leveraging the first individual's mobile device's current location to automatically direct the first individual to the address of an automatically selected healthcare provider or testing location. The selected healthcare provider or testing location can be determined based on wait times, proximity to the first individual's current location, facility capabilities, and other factors. In some implementations, the first individual's aggregated risk score can be ranked or otherwise compared to other individuals' aggregated risk scores. Individuals with higher risk scores can be prioritized for testing or other healthcare services over individuals with lower risk scores, thereby promoting efficient use of healthcare resources.

In some implementations, the digital health platform can facilitate integration of local bricks and mortar locations (e.g., pharmacies, groceries) that serve as distribution/collection points for medical diagnostic tests including specimen collection and drop-off. Inclusive of custom collection device delivery based on a bar code or kit code that is driven by the platform based on patient symptoms (e.g., pain on urination may indicate need for CTNG testing, but not HSV or syphilis testing unless certain other risk factors present). After the provider orders testing (or the app allows the user to select desired tests), the user would visit the pharmacy and scan a 2D barcode into a 'vending machine.' The machine would deliver only the kits required, based on the provider's orders or user's selections. This could also be accessible directly to external areas of the pharmacy, allowing for 24/7 access, and loading of kit materials from inside the building.

Figure 3:
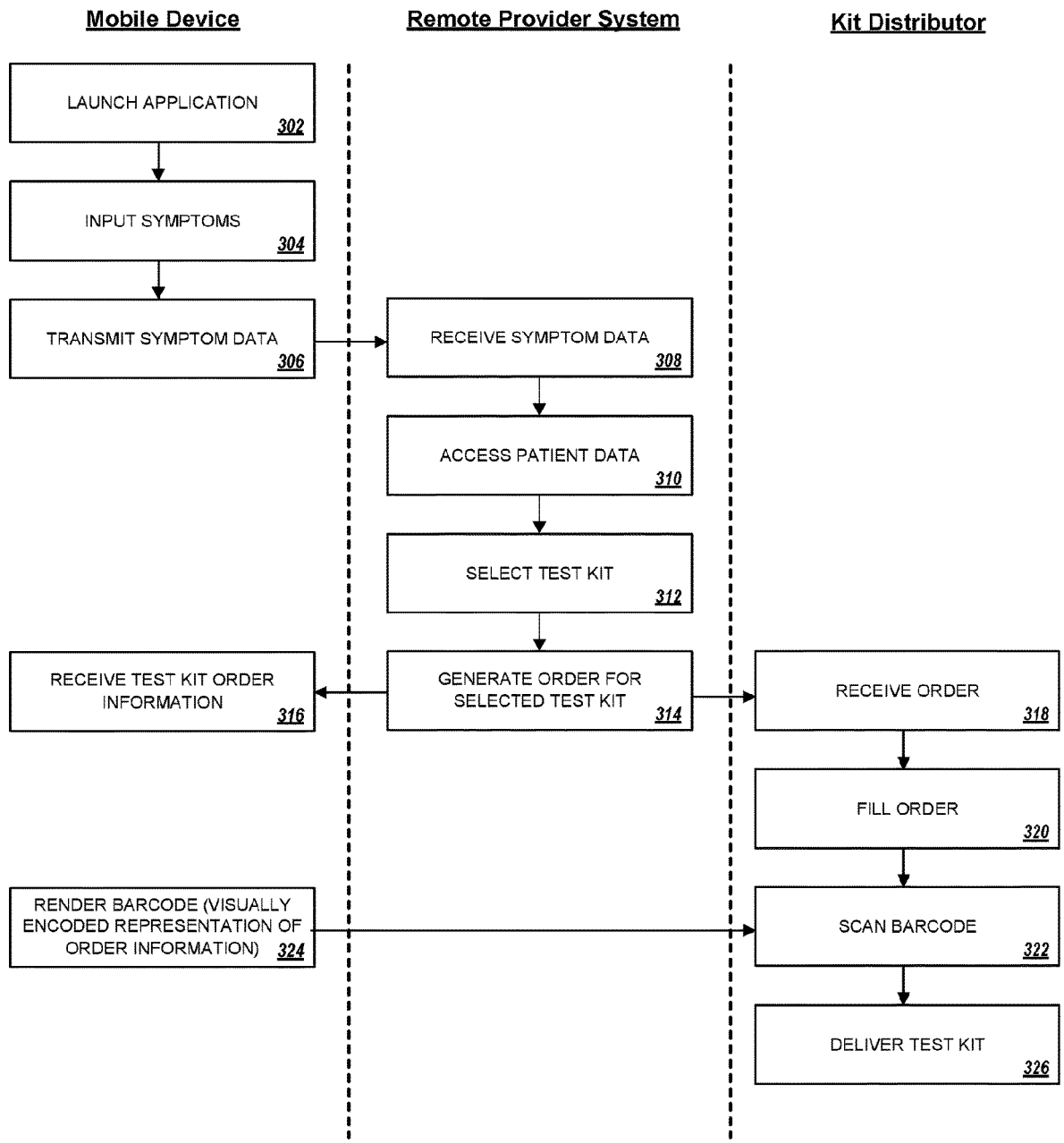
FIG. 3 is a swim-lane diagram of an example process for using the digital health platform to acquire a test kit corresponding to symptoms presented by a user.

FIG. 3 is a swim-lane diagram of an example process 300 for using the digital health platform to acquire a test kit corresponding to symptoms presented by a user. In some implementations, the process 300 can be carried out in whole or in part by systems and devices akin to those depicted in the computing environment 100 of FIG. 1. A user can launch an application that provides a portal to the health platform on his or her mobile device (302). The user inputs a description of symptoms related to a medical condition currently being exhibited (304), and the mobile device transmits the symptom data and patient information to a remove provider system (306-308). Upon receipt of the data, the remote service provider system accesses patient information with authorization from the patient (310) (e.g., medical history of the patient, demographic information of the patient, allergies of the patient). The remote service provider system automatically, or based on input from a healthcare provider (e.g., a pharmacist or physician), selects a test kit to test the patient for a particular condition (312). The particular test kit that is selected is based on the patient's described symptoms and any applicable information from the patient's medical history and other patient information. The remote service provider can then generate an order for the selected test kit (314). The order is sent to a kit distributor (e.g., a pharmacy) (318) and a confirmation of the order is sent to the patient's mobile device (316). The kit distributor can fulfill the order and make it available for pickup at a "vending machine'-style automated kiosk (320). For example, the user's mobile device may render the order confirmation as a 1D or 2D barcode on the display of the mobile device (324), and the barcode can be scanned (322) to permit the kit distributor machine to identify the selected kit that was prepared for the patient. The kit is then physically made available to the patient in an automated fashion (326).

Implementations of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal, which is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, general or special purpose microprocessors or both, or any other kind of central processing unit. Generally, a central processing unit will receive instructions and data from a read-only memory or a random access memory or both. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some implementations, a server transmits data, e.g., an HTML, page, to a user device, e.g., for purposes of displaying data to and receiving user input from a user interacting with the user device, which acts as a client. Data generated at the user device, e.g., a result of the user interaction, can be received from the user device at the server.

Figure 4:
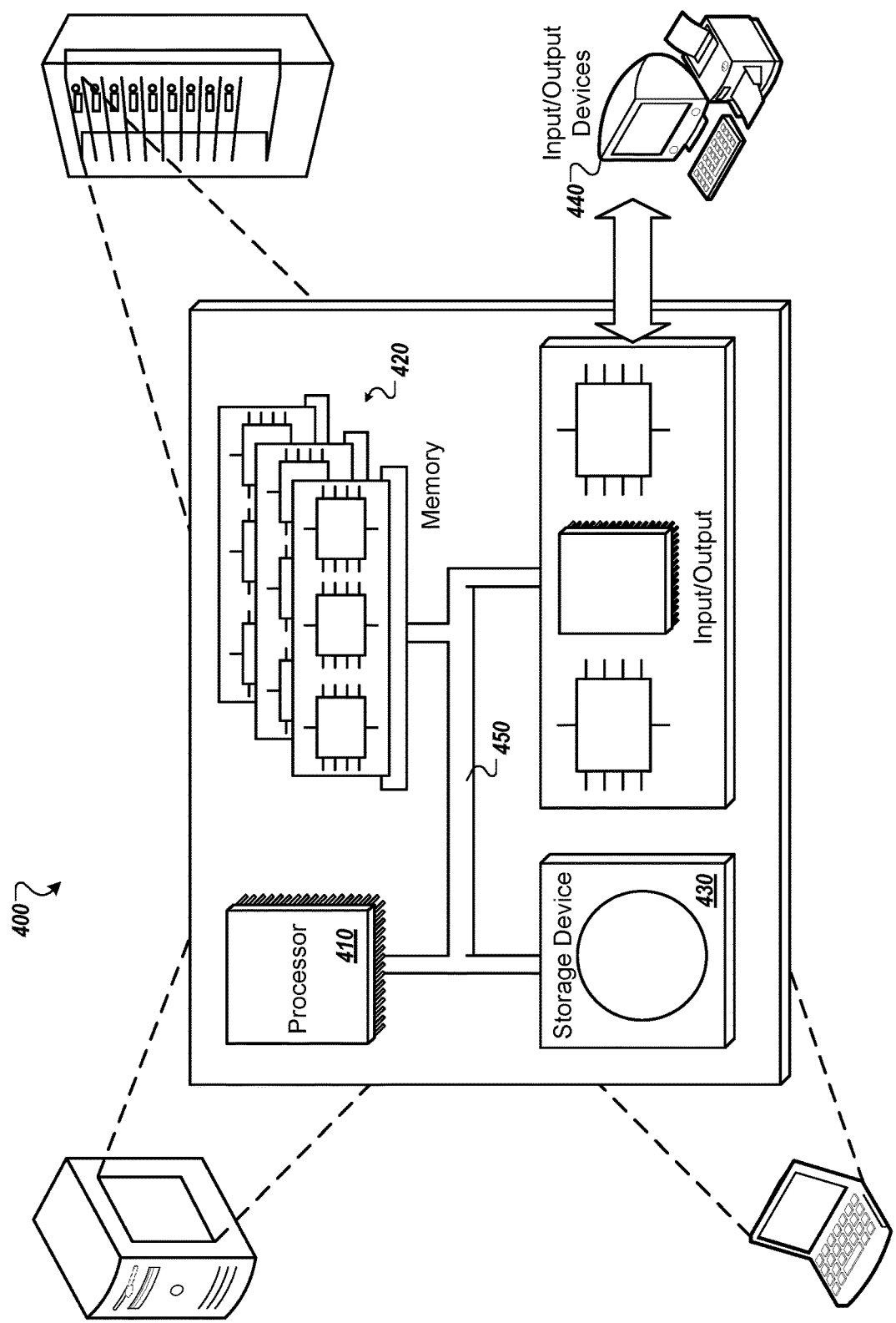
FIG. 4 is a block diagram of a computing system that can be used in connection with computer-implemented methods and other techniques described in this document.

An example of one such type of computer is shown in FIG. 4, which shows a schematic diagram of a generic computer system 400. The system can be used for the operations described in association with any of the computer-implemented methods described previously, according to one implementation. The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the system 400. In one implementation, the storage device 430 is a computer-readable medium. In various different implementations, the storage device 430 may be a floppy disk device, a hard disk device, an optical disk device, or a tape device.

The input/output device 440 provides input/output operations for the system 400. In one implementation, the input/output device 440 includes a keyboard and/or pointing device. In another implementation, the input/output device 440 includes a display unit for displaying graphical user interfaces.

While this specification contains many specific implementation details, these should not be construed as limitations on the scope of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations are within the scope of the following claims. For example, the actions recited in the claims can be performed in a different order consistent with logic and still achieve desirable results. As one example, the processes depicted in the accompanying figures do not necessarily require the particular order shown, or sequential order, to achieve desirable results. In some cases, multitasking and parallel processing may be advantageous.

Although various examples have been described in detail above, other modifications are possible. Accordingly, other implementations are within the scope of the following claims.

What is claimed is:

1. A method implemented by a mobile device for assessing a risk of exposure by a user of the mobile device to an infectious agent, comprising:
    detecting a first interaction between the user of the mobile device and a first individual encountered by the user of the mobile device by detecting, in real time, physical presence of the first individual in the vicinity of the user;
    storing information about the first interaction in memory of the mobile device, the stored information including first context data that describes a context of the first interaction between the user and the first individual;
    receiving, from an infection exposure database, an indication that the first individual was exposed to the infectious agent;
    computing, based on the stored information about the first interaction, a first interaction risk score that indicates an estimated risk of exposure by the user to the infectious agent as a result of the first interaction between the user and the first individual; and
    notifying the user of the exposure risk when the first interaction risk score meets a predetermined criteria.

2. The method of claim 1, further comprising:
    detecting a second interaction between the user of the mobile device and the user and a second individual encountered by the user of the mobile device by detecting, in real time, physical presence of the first or second individual in the vicinity of the user;
    storing information about the second interaction in memory of the mobile device, the stored information including second context data that describes a context of the second interaction between the user and the second individual;
    receiving, from an infection exposure database, an indication that the second individual was exposed to the infectious agent;
    computing, based on the stored information about the second interaction, a second interaction risk score that indicates an estimated risk of exposure by the user to the infectious agent as a result of the second interaction between the user and the first or second individual; and
    notifying the user of the exposure risk when the second interaction risk score meets a predetermined criteria.

3. The method of claim 2, further comprising:
    aggregating multiple interaction risk scores, including the first interaction risk score and the second interaction risk score, to determine an aggregated interaction risk score that indicates a cumulative risk of exposure by the user to the infectious agent as a result of multiple interactions; and
    notifying the user of the exposure risk when the aggregated interaction risk score meets a predetermined criteria.

4. The method of claim 2, further comprising:
    displaying the bar code for scanning by a test kit distributor; and
    receiving a test kit.

5. The method of claim 4, wherein the test kit distributor comprises a vending machine.

6. The method of claim 1, wherein the indications that the first individual was exposed to the infectious agent comprises an indication that the first individual has been infected by the infectious agent.

7. The method of claim 1, wherein the first context data comprises at least one of:
    mapping data that identifies one or more attributes of a location where the first interaction occurred;
    a physical distance between the user and the first individual during the first interaction; and
    a time duration of the first interaction with the first individual.

8. The method of claim 6, wherein the mapping data identifies at least one of a zoning classification for an area corresponding to the location where the first interaction occurred or a facility classification for a facility corresponding to the location where the first interaction occurred.

9. The method of claim 7, wherein the first interaction risk score is weighted based on the zoning classification and/or the facility classification.

10. The method of claim 1, wherein the first interaction risk score is weighted based on the distance associated with the first interaction.

11. The method of claim 1, wherein the first interaction risk score is weighted based on the duration of the first interaction.

12. The method of claim 1, wherein the first context data indicates a parameter that is based on when the user was exposed to the infectious agent, when the first individual tested positive for being infected by the infectious agent, or when the first individual presented one or more symptoms of being infected by the infectious agent.

13. The method of claim 1, wherein the context data indicates a health profile for the user, the health profile including at least one of demographic information for the user, an indication of co-morbidities exhibited by the user, or a health history of the user.

14. The method of claim 1, wherein detecting, in real time, physical presence of the first individual in the vicinity of the user comprises detecting a signal emitted by a device associated with the first individual.

15. The method of claim 1, further comprising providing a recommendation course of action to the user when the first interaction risk score meets the predetermined criteria.

16. The method of claim 1, further comprising receiving, test kit order information including a bar code encoded with test kit information.

17. A mobile device, comprising:
    processing circuitry;
    memory storing executable instructions that, when executed by the processing circuitry, causes the mobile device to:
        detect a first interaction between the user of the mobile device and a first individual encountered by the user of the mobile device by detecting, in real time, physical presence of the first individual in the vicinity of the user;
        store information about the first interaction in memory of the mobile device, the stored information including first context data that describes a context of the first interaction between the user and the first individual;
        receive, from an infection exposure database, an indication that the first individual was exposed to the infectious agent;
        compute, based on the stored information about the first interaction, a first interaction risk score that indicates an estimated risk of exposure by the user to the infectious agent as a result of the first interaction between the user and the first individual; and notify the user of the exposure risk when the first interaction risk score meets a predetermined criteria.

18. A non-transitory computer-readable media storing executable instructions that, when executed by processing circuitry in a mobile device, causes the mobile device to:
 detect a first interaction between the user of the mobile device and a first individual encountered by the user of the mobile device by detecting, in real time, physical presence of the first individual in the vicinity of the user;
 store information about the first interaction in memory of the mobile device, the stored information including first context data that describes a context of the first interaction between the user and the first individual;
 receive, from an infection exposure database, an indication that the first individual was exposed to the infectious agent;
 compute, based on the stored information about the first interaction, a first interaction risk score that indicates an estimated risk of exposure by the user to the infectious agent as a result of the first interaction between the user and the first individual; and
 notify the user of the exposure risk when the first interaction risk score meets a predetermined criteria.

* * * * *